United States Patent [19]

Fost et al.

[11] Patent Number: 5,623,043

[45] Date of Patent: Apr. 22, 1997

[54] SILICONE MODIFIED PHOSPHOLIPID COMPOSITIONS

[75] Inventors: Dennis L. Fost, Ridgewood; Abe Berger, Summit, both of N.J.

[73] Assignee: Mona Industries, Inc., Paterson, N.J.

[21] Appl. No.: 420,748

[22] Filed: Apr. 12, 1995

Related U.S. Application Data

[63] Continuation-in-part of Ser. No. 174,660, Dec. 28, 1993, abandoned, and a continuation-in-part of Ser. No. 298,565, Aug. 31, 1994, abandoned.

[51] Int. Cl.$^6$ .................................................. C08G 77/04
[52] U.S. Cl. ................... 528/26; 528/25; 528/38; 548/406
[58] Field of Search ............................ 528/25, 26, 38; 548/406

[56] References Cited

U.S. PATENT DOCUMENTS

| | | |
|---|---|---|
| 2,488,449 | 11/1949 | Trautman . |
| 2,768,193 | 10/1956 | Gilbert . |
| 2,843,615 | 7/1958 | Linville . |
| 3,067,229 | 12/1962 | Fekete . |
| 3,441,537 | 4/1969 | Lengnick . |
| 3,839,388 | 10/1974 | Nitzsche et al. . |
| 4,006,176 | 2/1977 | Heckert . |
| 4,093,641 | 6/1978 | Plueddemann . |
| 4,185,087 | 1/1980 | Morlino . |
| 4,898,614 | 2/1990 | Halloran et al. . |
| 5,070,171 | 12/1991 | O'Lenick, Jr. . |
| 5,091,493 | 2/1992 | O'Lenick, Jr. et al. . |
| 5,093,452 | 3/1992 | O'Lenick, Jr. . |
| 5,099,051 | 3/1992 | Beck et al. . |
| 5,101,056 | 3/1992 | Kampling et al. . |

*Primary Examiner*—Melvyn I. Marquis
*Attorney, Agent, or Firm*—Franklyn Schoenberg

[57] ABSTRACT

A silicone-containing phospholipid composition is provided having the general formula:

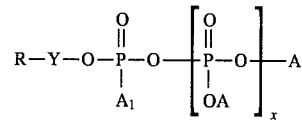

wherein:

A can be H, M or R—Y—; $A_c$ can be H, OH, OM or R—Y—O; $A_1$ is selected from H, OH, OM or R—Y—O—; M is a cation; Y is alkylene or substantially alkylene; x is 0 or an integer from 1–5; and R is a quaternized organosilicone amidoamine reactant moiety of the formula:

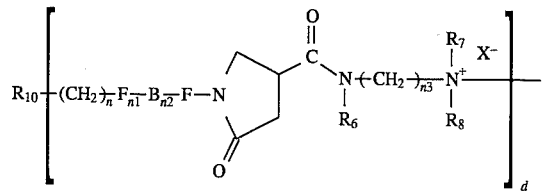

wherein:

$R_{10}$ is the silicone backbone chain to which at least one pyrrolidone containing amidoamine functional group is attached;

$R_6$ is hydrogen, alkyl, hydroxyalkyl, alkenyl cycloalkyl or polyoxyalkylene;

$R_7$ and $R_8$ are selected from alkyl, hydroxyalkyl, carboxyalkyl and polyoxyalkylene;

F is linear or branched alkylene; $X^-$ is an anion; n is 0 or 2; $n^1$ is 0 or 1; $n^2$ is 0 or 1; $n^3$ is an integer from 2 to 12. B is —$NR_{11}$ sulfur or oxygen, wherein R11 is hydrogen or lower alkyl; with the proviso that when $n^1$ is 0 and $n^2$ is 1, $n^1$ is 1, when n is 2 and $n^2$ is 1, $n^1$ is 0 or 1 and when n is 2 and $n^2$ is 0, $n^1$ is 0; and; d is one or greater.

17 Claims, No Drawings

SILICONE MODIFIED PHOSPHOLIPID COMPOSITIONS

RELATED APPLICATIONS

This application is a continuation in part of application Ser. No. 174,660, filed Dec. 28, 1993, now abandoned, and application Ser. No. 298,565 filed Aug. 31, 1994, now abandoned.

FIELD OF THE INVENTION

The present invention relates to novel organosilicone compositions and, more particularly, to silicone compositions having a carboxyl functional group thereon and to derivatives thereof having at least one esterified phosphate group in the molecule.

BACKGROUND OF THE INVENTION

Phosphate esters, quaternary ammonium compounds, betaines and certain substituted betaines are known in the art and have been commercially used over the years for a variety of applications, including those requiring surfactant properties. More recently, various betaine derivatives having, in general, specific quaternary compounds linked to phosphate esters referred to as phosphobetaines, and more particularly "synthetic phospholipids," have been disclosed, for example, in U.S. Pat. Nos. 4,215,064, 4,233,192 and 4,380,637 to Lindemann et al.; 4,209,449, 4,336,385 and 4,503,002 to Mayhew et al.; 4,243,602, 4,283,542 and 4,336,386 to O'Lenick et al; and 4,617,404 to Lukenbach et al. These synthetic phospholipids are disclosed as exhibiting outstanding foaming, viscosity building, wetting, cleansing, detergency, anti-static, conditioning and emulsifying properties, making them useful in industrial applications calling for high performance surface active agents. The synthetic phospholipids are also described as being highly stable compounds which are well tolerated by human tissue (i.e. they exhibit exceptionally low oral toxicity and ocular irritation) and, hence, are well suited for use in a variety of personal care applications including cosmetic formulations as well as in industrial processes.

A variety of organosiloxane compositions including compositions which exhibit excellent properties as surface active agents, lubricants and the like are known and have been used commercially over the years, including for personal care and home care applications. In general, however, organosiloxane compositions are water insoluble, which has limited their use for many applications. Recently, particular types of betaine and phosphobetaine modified organosiloxanes having improved, although limited water solubility properties have been disclosed, for example, in U.S. Pat. Nos. 4,609,750 and 4,654,161 to Kollmeier et al. and U.S. Pat. No. 5,091,493 to O'Lenick et al. Such compositions are suggested as exhibiting high foaming characteristics in water, substantivity to a variety of surfaces and reduced irritation to the eyes and skin. While, as indicated, certain organosilicone containing phosphobetaine compositions and methods for preparing the same heretofore have been suggested, there has been no disclosure or suggestion of the novel carboxyl functional silicone compositions and silicone-containing phospholipid compositions described in copending application Ser. No. 174,680 and Ser. No. 298,565 of which the present applications is a continuation in part, or of the novel silicone-containing phospholipid compositions and methods for preparing the same herein described, which compositions exhibit a wide range of properties including solubility in a variety of solvents, preferably water, and are useful for a variety of different applications.

SUMMARY OF THE INVENTION

It is accordingly an object of the present invention to provide novel silicone-containing compositions which exhibit improved solubility characteristics particularly improved aqueous solubility.

It is another object of the present invention to provide novel silicone-containing phospholipid compositions which exhibit excellent surface-active properties including high foaming, are well tolerated by human tissue, are substantive to the surface of a variety of substrates such as fiber, and the like.

It is a further object of the present invention to provide novel soluble, preferably water soluble silicone-containing phospholipid compositions having functional phophorous containing groups linked terminally, laterally, or combination(s) of terminal and lateral linkages to the polysiloxane, which compositions can be prepared with a variety of concentrations of silicone, as desired or required.

It is still another object of the present invention to provide novel silicone-containing phospholipid compositions which exhibit improved aqueous solubility characteristics and can be prepared with varying concentrations of silicones as desired by reactions with halogen containing phosphate, phosphite or polyphosphate, ester reactants.

In accordance with the present invention, there has now been discovered novel silicone containing phospholipid compositions that may be represented by the following general formula:

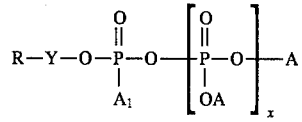

wherein:
A is selected from H, M and R—Y—;
$A_1$ is selected from H, OH, OM and R—Y—O—;
x is 0 or an integer from 1 to 5;
M is a cation, preferably an alkali metal;
Y is a alkylene or substituted alkylene; and
R is a quaternized organosilicone amidoamine reactant moiety of the formula:

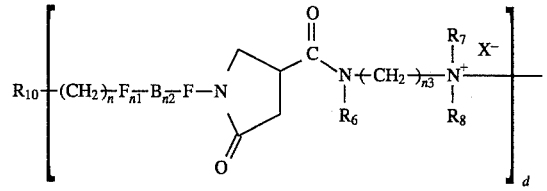

wherein:
$R_{10}$ is the silicone backbone chain to which a pyrrolidone containing carboxyl or ester functional group or amidoamine derivative thereof as herein described can be attached as shown;
$R_6$ is hydrogen or alkyl, hydroxyalkyl or alkenyl of up to 6 carbon atoms, cycloalkyl of up to 6 carbon atoms, or polyoxyalkylene of up to 10 carbon atoms, preferably from 2 to 5 carbon atoms, within the oxyalkylene unit;

$R_7$ and $R_8$, which may be the same or different, are selected from alkyl, hydroxyalkyl, carboxyalkyl of up to 6 carbon atoms in each alkyl moiety and polyoxyalkylene of up to 10 carbon atoms; in addition $R_7$ and $R_8$ taken together with the nitrogen to which they are attached may represent an N-heterocycle;

F, which can be the same or different, is linear or branched alkylene of 1–12 carbon atoms;

$X^-$ is an anion, preferably a halogen;

n is 0 or 2;

$n^1$ is 0 or 1;

$n^2$ is 0 or 1;

$n^3$ is an integer from 2 to 12;

B is $-NR_{11}$, sulfur (S) or oxygen (O), wherein $R_{11}$ is hydrogen or lower alkyl ($C_{1-6}$) with the proviso that when n is 0 and $n^2$ is 1, $n^1$ is 1, when n is 2 and $n^2$ is 1, $n^3$ is 0 or 1, and when n is 2 and $n^2$ is 0, $n^1$ is 0; and d is one or greater, preferably 2–10

In a further aspect of the present inventions there is provided novel silicone-containing phospholipid compositions that may be represented by the following general formula:

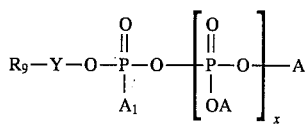

wherein:

A is selected from H, M and R—Y—;

$A_1$ is selected from H, OH, OM and R—Y—O—;

M is a cation, preferably an alkali metal;

x is 0 or an integer from 1 to 5;

Y is alkylene or substituted alkylene; and $R_9$ is a mixture of quaternized silicone-containing amidoamine, organic amidoamine and/or organic tertiary amine moieties selected from the group consisting of:

a) a quaternized organosilicone amidoamine moiety of the formula:

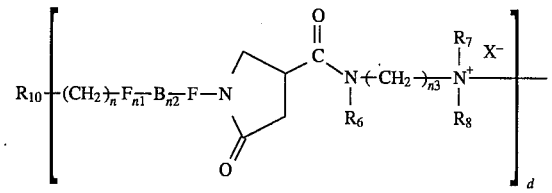

wherein:

$R_{10}$ is a silicone backbone chain to which a pyrrolidone containing carboxyl or ester functional group or amido amine derivative thereof as hereinafter described can be attached;

$R_6$ is hydrogen or alkyl, hydroxyalkyl or alkenyl of up to 6 carbon atoms, cycloalkyl of up to 6 carbon atoms, or polyoxyalkylene of up to 10 carbon atoms, preferably from 2 to 5 carbon atoms, within the oxyalkylene unit;

$R_7$ and $R_8$, which may be the same or different, are selected from alkyl, hydroxyalkyl, carboxyalkyl of up to 6 carbon atoms in each alkyl, and polyoxyalkylene of up to 10 carbon atoms; in addition $R_7$ and $R_8$ taken together with the nitrogen to which they are attached may represent an N-hetercycle.

F, which can be the same or different, is linear or branched alkylene of 1–12 carbon atoms;

$X^-$ is an anion, preferably a halogen;

n is 0 or 2;

$n^1$ is 0 or 1;

$n^2$ is 0 or 1;

$n^3$ is an integer from 2 to 12;

B is $-NR_{11}$, sulfur (S) or oxygen (O) wherein $R_{11}$ is hydrogen or lower alkyl ($C_{1-6}$); with the proviso that when n is 0 and $n^2$ is 1, $n^1$ is 1, when n is 2 and $n^2$ is 1, $n^1$ is 0 or 1 and when n is 2 and $n^2$ is 0, $n^1$ is 0; and d is one or greater, preferably 2–10;

b) a quaternized organic amidoamine moiety of the formula:

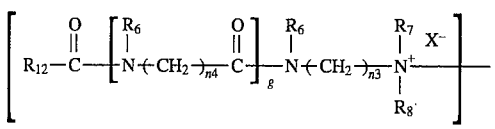

wherein:

$R^{12}$ is alkyl, alkenyl, alkoxy or hydroxyalkyl of from 5 to 21 carbon atoms each, alkaryl or aryl of up to 20 carbon atoms;

$R_6$ is hydrogen or alkyl, hydroxyalkyl or alkenyl of up to 6 carbon atoms, cycoalkyl of up to 6 carbon atoms, or polyoxyalkylene of up to 10 carbon atoms, preferably of from 2 to 5 carbon atoms, within the oxyalkylene unit;

$R_7$ and $R_8$ which may be the same or different, are selected from alkyl, hydroxyalkyl, carboxyalkyl of up to 6 carbon atoms in each alkyl moiety, and polyoxyalkylene of up to 10 carbon atoms; in addition $R_7$ and $R_8$ taken together with the nitrogen to which they are attached may represent an N-heterocycle;

$X^-$ is an anion, preferably a halogen;

g is 0 or 1;

$n^3$ is integer from 2 to 12; and $n^4$ is 1 or greater; and c) an organic quaternized tertiary amine moiety of the formula:

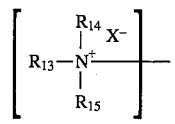

wherein:

$R_{13}$, $R_{14}$ and $R_{15}$ are the same or different and are alkyl, substituted alkyl, alkyl aryl or alkenyl groups of up to 16 carbon atoms with the proviso that the total carbon atoms in $R_{13}+R_{14}+R_{15}$ is between 10 and 24;

with the proviso that at least 5 equivalent weight percent to about 70 equivalent weight percent of the total equivalent weight of amine moieties of the phospholipid composition is a quaternized organosilicone amidoamine moiety.

It is evident from the general phospholipid formulae above that the functional phosphorus containing group(s) can be linked terminally, laterally or both terminally and laterally to the polysiloxane chain through the amidoamine and/or tertiary amine functional group.

In a still further aspect of the present invention there is provided a method of preparing novel phospholipid compositions that may be represented by the general formula:

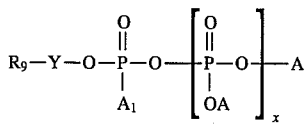

wherein:

A is selected from H, M and R—Y—;

$A_1$ is selected from H, OH, OM and R—Y—O—;

Y is alkylene or substituted alkylene;
M is a cation, preferably an alkali metal;
x is 0 or an integer from 1 to 5; and
$R_9$ is a mixture of quaternized amidoamine and/or tertiary amine moieties as hereinabove defined;

which comprises reacting the combination of an organic amidoamine and/or organic tertiary amine reactant and a silicone-containing amidoamine reactant with a polyphosphate, phosphite or phosphate ester halide reactant in the equivalent weight ratios of from about 0.7 to 3.3 of total amidoamine and/or tertiary amine reactants to 1 of polyphosphate, phosphite or phosphate ester halide reactant until the amine reactant is completely reacted, with the proviso that at least 5 equivalent weight percent to about 70 equivalent weight percent of the total equivalent weight of amine reactants will be silicone containing, said polyphosphate, phosphite or phosphate ester halide reactant being of the general formula:

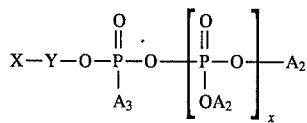

wherein:
$A_2$ is selected from H, M and X—Y—;
$A_3$ is selected from H, OH, OM and R—Y—O—;
x is 0 or an integer from 1 to 5;
M is a cation, preferably alkali metal;
Y is alkylene or substituted alkylene; and
X is halogen.

DESCRIPTION OF THE PREFERRED EMBODIMENTS

In accordance with the present invention, there are provided novel phospholipid compositions which comprise a class of silicone-containing phospholipid compositions represented by the general formula:

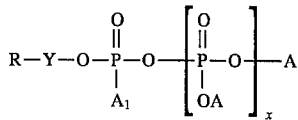

wherein:
A is selected from H, M and R—Y—;
$A_1$ is selected from H, OH, OM and R—Y—O—;
x is 0 or an integer from 1 to 5;
M is a cation, preferably an alkali metal;
Y may be alkylene, optionally interrupted by up to 3 oxygen atoms, of up to 12 carbon atoms, which alkylene chain may optionally be substituted with lower alkyl, alkoxyalkyl or hydroxyalkyl, e.g. not more than 10 carbon atoms each; and
R is a novel quaternized organosilicone amidoamine reactant moiety of the formula:

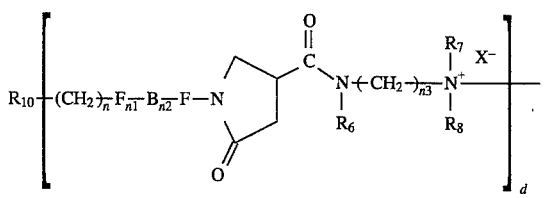

wherein:
$R_{10}$ is the silicone backbone chain to which at least one pyrrolidone containing carboxyl or ester functional group or amidoamine derivative thereof is attached as herein described;
$R_6$ is hydrogen or alkyl, hydroxyalkyl or alkenyl of up to 6 carbon atoms each, cycloalkyl of up to 6 carbon atoms, or polyoxyalkylene of up to 10 carbon atoms, preferably from 2 to 5 carbon atoms, within the oxyalkylene unit;
$R_7$ and $R_8$, which may be the same or different, are selected from alkyl, hydroxyalkyl, carboxyalkyl of up to 6 carbon atoms in each alkyl and polyoxyalkylene of up to 10 carbon atoms; in addition $R_7$ and $R_8$ taken together with the N to which they are attached may represent an N-hetercycle.
F, which can be the same or different, is a linear or branched alkylene of 1–12 carbon atoms;
$X^-$ is an anion, preferably a halogen;
n is 0 or 2;
$n^1$ is 0 or 1;
$n^2$ is 0 or 1;
$n^3$ is an integer from 2 to 12;
B is, —$NR_{11}$, sulfur (S) or oxygen (O), wherein $R_{11}$ is H or a lower alkyl ($C_{1-6}$); with the proviso that when n is 0 and $n^2$ is 1, $n^1$ is 1, when n is 2 and $n^2$ is 0, $n^1$ is 0 or 1 and when n is 2 and $n^2$ is 0, $n^1$ is 0; and
d is one or greater, preferably 2–10.

In an alternate embodiment of the present invention, there are also provided novel phospholipid compositions including high molecular weight polysiloxanes which comprise a class of silicone-containing phospholipid compositions which exhibit a surprising and unexpected solubility in aqueous systems and/or aqueous/co-solvent systems. Such novel silicone-containing phospholipid compositions may be represented by the general formula:

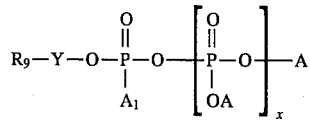

wherein:
A is selected from H, M and R—Y—;
$A_1$ is selected from H, OH, OM and R—Y—O—;
M is a cation, preferably an alkali metal;
x is 0 or an integer from 1 to 5;
Y may be alkylene optionally interrupted by up to 3 oxygen atoms, of up to 12 carbon atoms which alkylene chain may optionally be substituted with lower alkyl, alkoxyalkyl or hydroxyalkyl, e.g. not more than 10 carbon atoms each; and
$R_9$ is a mixture of quaternized amidoamine and/or tertiary amine moieties selected from the group consisting of:
a) a quaternized organosilicone amidoamine moiety of the formula:

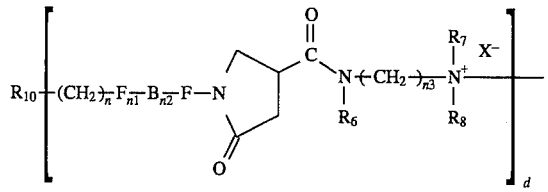

wherein:
$R_{10}$ is a silicone backbone chain to which at least one pyrrolidone containing carboxyl or ester functional group or amidoamine derivative thereof as herein described can be attached;

$R_6$ is hydrogen or alkyl, hydroxyalkyl or alkenyl of up to 6 carbon atoms each, or cycloalkyl of up to 6 carbon atoms, or polyoxyalkylene of up to 10 carbon atoms, preferably from 2 to 5 carbon atoms, within the oxyalkylene unit;

$R_7$ and $R_8$, which may be the same or different, are selected from alkyl, hydroxyalkyl, carboxyalkyl of up to 6 carbon atoms in each alkyl, and polyoxyalkylene of up to 10 carbon atoms; in addition $R_7$ and $R_8$ taken together with the N to which they are attached may represent an N-hetercycle;

$X^-$ is an anion, preferably a halogen;

n is 0 or 2;

$n^1$ is 0 or 1;

$n^2$ is 0 or 1;

$n^3$ is an integer from 2 to 12;

B is $-NR_{11}$, sulfur (S) or oxygen (O), wherein $R_{11}$ is hydrogen or lower alkyl; with the proviso that when n is 0 and $n^2$ is 1, $n^1$ is 1, when n is 2 and $n^2$ is 1, $n^2$ is 0 or 1 and when n is 2 and $n^1$ is 0, $n^1$ is 0; and d is one or greater, preferably 2–10;

b) a quaternized organic amidoamine moiety of the formula:

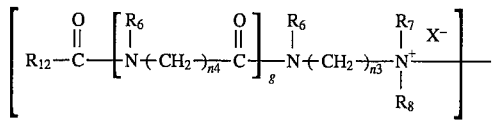

wherein:

$R_{12}$ is alkyl, alkenyl, alkoxy or hydroxyalkyl of from 5 to 21 carbon atoms each, alkaryl or aryl of up to 20 carbon atoms;

$R_6$ is hydrogen or alkyl, hydroxyalkyl or alkenyl of up to 6 carbon atoms each, cycoalkyl of up to 6 carbon atoms, or polyoxyalkylene of up to 10 carbon atoms, preferably of from 2 to 5 carbon atoms, within the oxyalkylene unit;

$R_7$ and $R_8$ which may be the same or different, are selected from alkyl, hydroxyalkyl, carboxyalkyl of up to 6 carbon atoms in each alkyl moiety, and polyoxyalkylene of up to 10 carbon atoms; in addition $R_7$ and $R_8$ taken together with the nitrogen to which they are attached may represent an N-heterocycle;

$X^-$ is an anion, preferably a halogen;

g is 0 or 1;

$n^3$ is integer from 2 to 12; and $n^4$ is 1 or greater; and c) an organic quaternized tertiary amine moiety of the formula:

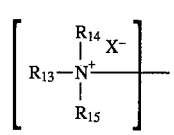

wherein:

$R_{13}$, $R_{14}$ and $R_{15}$ are the same or different and are alkyl, substituted alkyl, alkyl aryl or alkenyl groups of up to 16 carbon atoms with the proviso that the total carbon atoms in $R_{13}+R_{14}+R_{15}$ is between 10 and 24;

$X^-$ is an anion, preferably a halogen;

with the proviso that at least 5 equivalent weight percent to about 70 equivalent weight percent of the total equivalent weight of amine moieties of the phospholipid composition is a quaternized organosilicone amidoamine moiety.

Preferred silicone-containing phospholipid compositions of the invention wherein Y is 2-hydroxypropylene comprise a class of compositions which may be represented by the general formule;

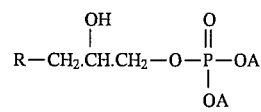

and

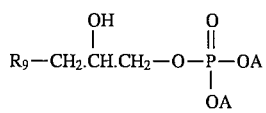

wherein

A, R and $R_9$ are as defined above.

The silicone backbone chain $R_{10}$ to which the pyrrolidone containing amidoamine functional group hereinabove shown (represented below as $R_1$) are attached corresponds to the general formula:

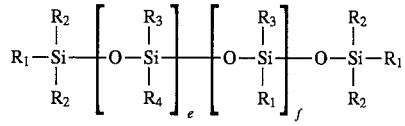

wherein:

$R_1$, which can be the same or different, can be selected from $R_2$, a primary amine and a pyrrolidone containing group of the formula:

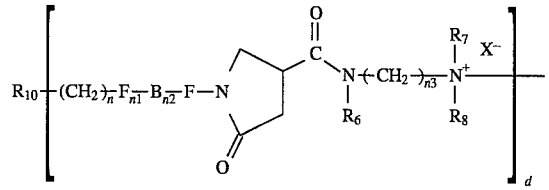

wherein at least one of $R_1$ is a pyrrolidone containing amidoamine functional group as shown; F, which can be the same or different is a linear or branched alkylene of 1–12 carbon atoms; $R_2$ is as defined below; $R_7$ and $R_8$ which may be the same or different are selected from alkyl, hydroxyalkyl, carboxyalkyl of up to 10 carbon atoms; in addition $R_7$ and $R_8$ taken together with the nitrogen to which they are attached may represent N-heterocycle; n is 0 or 2; $n^1$ is 0 or 1; $n^2$ is 0 or 1; $n^3$ is an integer from 2 to 12; and B is $-NR_{11}$, sulfur (S) or oxygen (O), wherein $R_{11}$ is hydrogen or lower alkyl ($C_{1-6}$); with the proviso that when n is 0 and $n^2$ is 1, $n^1$ is 1, when n is 2 and $n^2$ is 1, $n^1$ is 0 or 1, and when n is 2 and $n^2$ is 0, $n^1$ is 0;

$R_2$ can be the same or different and can be selected from alkyl, aryl and olefinic (vinyl);

$R_3$ and $R_4$, which may be the same or different, are selected from alkyl, aryl, capped or uncapped polyoxyalkylene, alkaryl, aralkylene and alkenyl (vinyl);

e can be an integer from 0 to 50,000; and f can be an integer from 0 to 100.

It is evident from the general formulae of the novel phospholipid compositions of the invention that the functional phosphorus containing group(s) can be linked terminally, laterally or both terminally and laterally to the siloxane chain through the amidoamine functional containing alkylene and/or alkylene containing heteroatom group.

In accordance with the invention, the phospholipid compositions of the invention can be prepared by reacting corresponding silicone containing amidoamine reactants or alternatively, combinations of silicone containing amidoamine and organic amidoamine and/or tertiary amine reactants with phosphate, polyphosphate or phosphite ester halide reactants in appropriate stoichiometric quantities as will be described in detail hereinafter to obtain the desired products of the formulae:

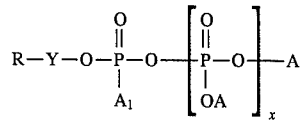

and

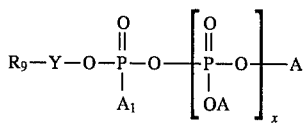

and preferably

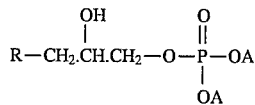

or

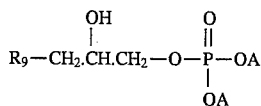

wherein:
A is as defined hereinabove;
$A_1$ is as defined hereinabove;
Y is as defined hereinabove;
x is as defined hereinabove;
M is as defined hereinabove; and
R is a quaternized organosilicone amidoamine moiety as defined hereinabove or, alternatively,
$R_9$ is a mixture of moieties selected from the group consisting of a quaternized organosilicone amidoamine moiety, quaternized organic amidoamine and/or organic quaternized tertiary amine moiety as defined hereinabove;
with the proviso that at least 5 equivalent weight percent to about 70 equivalent weight percent of the total equivalent weight of amine moieties of the phospholipid composition is a quaternized organosilicone amidoamine moiety.

The intermediate reactants required in the processes for preparing the silicone-modified phospholipid compounds of the invention can be prepared as described hereinafter.

Phosphate, polyphosphate and/or phosphite ester intermediate reactants suitable for use can be prepared by known procedures illustrated as follows:

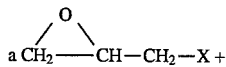

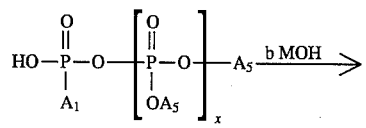

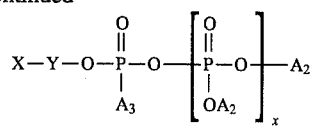

wherein:
$A_2$ is selected from H, M and X—Y—;
$A_3$ is selected from H, OH, OM and X—Y—O—;
$A_4$ is H, OM or OH;
$A_5$ is H or M;
a is from 0.5 to 3.5. preferably 1 to 3;
b is from 1 to 3; preferably 1 to 2;
M is a cation, preferably an alkali metal;
x is 0 or an integer from 1 to 5;
X is halogen; and
Y is 2-hydroxypropylene.

The above coupling reaction (I) is carried out in all aqueous media, preferably in the range of 30–50% concentration, having a pH range of 5.0–8.0.

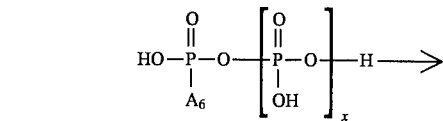

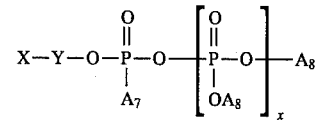

wherein:
$A_6$ is selected from H or OH;
$A_7$ is selected from H, OH or X—Y—O—;
$A_8$ is H or —Y—X;
a is from 0.5 to 7, preferably from about 1 to 3;
x is 0 or an integer from 1 to 5;
X is halogen; and
Y is 2-hydroxypropylene.

The above reaction (II) is preferably carried out in the absence of water.

Phosphate, phosphite and polyphosphate ester halide intermediate reactants for preparing phosphobetaine, pyrophospobetaine and the like compositions of the invention can also be prepared by known procedures such as disclosed, for example, in U.S. Pat. No. 4,617,414.

Also suitable as phosphate and phosphite intermediate halide reactants are such reactants prepared by known procedures illustrated as follows:

(3-a) X—$R_{16}$—OH + POCl$_3$ ⟶  III (a)

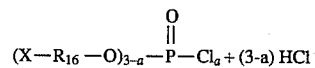   III (b)

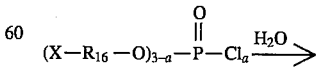

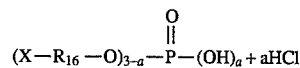

wherein:
a is 0 or an integer from 1 to 2;

X is halogen; preferably bromine; and
R$_{16}$ is alkylene.

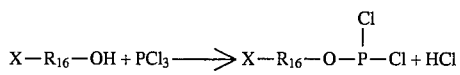

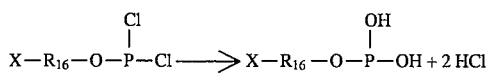

wherein:
X is a halogen; preferably bromine; and
R$_{16}$ is alkylene.

Carrying out reactions III(a) and IV(b) in the presence of a teritary amine HCl acceptor is preferred to prevent any secondary reaction with the generated HCl gas.

Silicone-containing amidoamines suitable for use as intermediate reactants in preparing the phospholipid compositions of the invention can be prepared as follows:

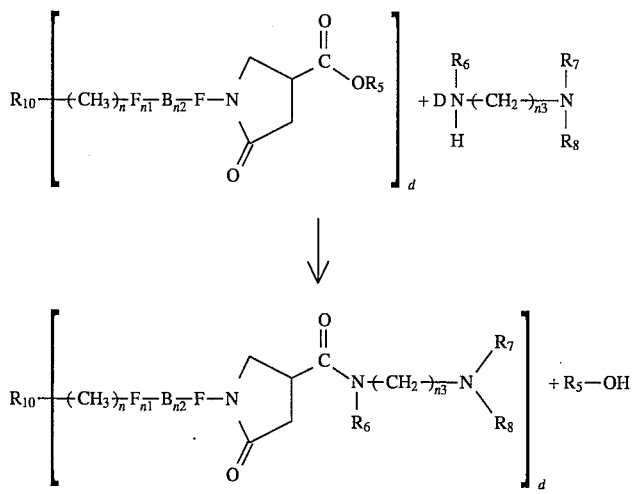

wherein:
R$_{10}$ is a silicone backbone chain to which at least one pyrrolidone containing carboxyl or ester functional group or amidoamine derivative thereof is attached as hereinabove shown;
R$_5$ is hydrogen, lower alkyl (C$_{1-6}$) or alkali metal;
R$_6$ is hydrogen or alkyl, hydroxyalkyl or alkenyl up to 6 carbon atoms each, cycloalkyl of up to 6 carbon atoms or polyoxyalkylene of up to 10 carbon atoms, preferably from 2 to 5 carbon atoms, within the oxyalkylene unit and at least one R$_6$ is hydrogen;
F, which can be the same or different is linear or branched alkylene of 1–12 carbon atoms;
R$_7$ and R$_8$, which may be the same or different, are selected from alkyl, hydroxyalkyl, carboxyalkyl of up to 6 carbon atoms in each alkyl and polyoxyalkylene of up to 10 carbon atoms; in addition R$_7$ and R$_8$ taken together with the nitrogen to which they are attached may represent an N-hetercycle.
B is —NR$_{11}$, sulfur or oxygen wherein R$_{11}$ is hydrogen or lower alkyl (C$_{1-6}$); with the proviso that when n is 0 and n$^2$ is 1, n$^1$ is 1, when n is 2 and n$^2$ is 1, n$^1$ is 0 or 1 and when n is 2 and n$^2$ is 0, n$^1$ is 0;
n is 0 or 2;
n$^1$ is 0 or 1;
n$^2$ is 0 or 1;
n$^3$ is an integer from 2 to 12;

d and D is an integer from 1 or greater, generally from 1–50 and preferably 2–10. The reactant ratio of the amine reactant to the carboxyl reactant on the silicon is preferably 1:1 but can be varied in ratio from 1:0.8 to 1:1.2.

Silicone-containing amidoamines suitable for use as intermediate reactants are, thus, readily prepared by the above coupling reaction (V) from the novel polysiloxane compositions having one or more pyrrolidone containing functional carboxyl or ester group(s) as herein described.

The above coupling reaction (V) for preparing the silicone-containing amidoamine intermediate can be carried out neat or can be carried out in an inert solvent such as xylene, toluene, chlorobenzene or the like. While the equivalent weight of suitable silicone-modified intermediate amidoamine reactants is not critical, preferably the equivalent weight of such reactants is from about 500 to 1500.

The novel carboxyl functional polysiloxanes or derivatives thereof (terminal, lateral or combinations of terminal and lateral) applicable for use in preparing the silicone-containing amidoamine intermediate reactants of the invention as set forth in the reaction sequence (V) illustrated above can be prepared by procedures such as disclosed in parent application Ser. No. 298,565, filed Aug. 31, 1994 and in the application Ser. No. 420,746 filed concurrently herewith. Such procedures include the reaction of corresponding silicone compositions or fluids having one or more functional primary amine groups with up to about one equivalent, preferably about stoichiometric quantities, of itaconic acid or its ester per functional amine group at an elevated temperature for the time sufficient for substantially all of the itaconic acid or its ester to react with the functional primary amine group(s). Preferably, from about 0.9 to about 1.1 equivalents of itaconic acid or its ester per functional primary amine group is reacted with the silicone fluid wherein substantially all itaconic acid is reacted with the functional primary amine group(s) and polysiloxane compositions with at least one pyrrolidone containing functional carboxyl group(s) and/or its ester are formed.

The reaction can be carried out neat or in an inert solvent such as alcohol, hydrocarbon solvent, chlorinated hydrocarbon and the like, in general, at elevated temperature, preferably from about 90° C. to about 130° C. The reaction proceeds readily and generally complete reaction of the itaconic acid or its ester with the available functional primary amine groups will occur in from about 1 to 5 hours, with routine analytical techniques for amine and acid values as well as monitoring water and/or alcohol evolution being used to determine completion of the reaction.

Primary amine functional silicone fluids suitable for use having one or more primary amine functional group(s) linked terminally, laterally or both terminally and laterally, are well known and are available commercially, for example, from Dow Corning, Th. Goldschmidt AG and Shin-Etsu. While the equivalent weight of the silicone fluids or compositions which may be employed in the preparation of the pyrrolidone containing carboxyl functional polysiloxanes is not critical, and suitable compositions may have equivalent weights of 5,000 or even higher, silicone fluids having equivalent weights from about 500 to about 1500 are in general preferred.

As indicated, the polysiloxanes compositions are readily prepared by reaction of primary amine functional silicone fluids with itaconic acid or its ester. Itaconic acid (methylene succinic acid) is a compound of the formula:

$$CH_2=C(COOR_{11})CH_2COOR_{11}$$

wherein:

$R_{11}$, which can be the same or different is hydrogen or lower alkyl $(C_{1-6})$.

The compound is available commercially from Pfizer Chemicals Division and from Norflex, Inc., Greensboro, N.C. and is produced by known fermentation techniques although chemical synthesis methods are also known.

As noted above, silicone-containing phospholipid compositions of the invention can be prepared by reacting the desired silicone-containing amidoamine and phosphate, phosphite and/or polyphosphate ester halide reactants in appropriate desired stoichiometric proportions, in general, in molar equivalents of from about 0.7 to 3.3 of the amidoamine functional silicone reactant to 1 of the phosphate ester halide reactant. Such reaction can be carried out in a water solution or in conjunction with a co-solvent such as isopropyl alcohol, ethylene glycol, propylene glycol, ethyl cellosolve or the like. The reaction is carried out generally at elevated temperatures up to about 100° C., preferably from about 75° to 95° C., for a time ranging from about 1 to 5 hours, and generally until the amidoamine is substantially completely reacted. The course of the reaction can be determined by alkali number titration, ionic chloride determination, etc.

The reaction of the silicone-containing amidoamine and phosphate, phosphite and/or polyphosphate ester halide reactants can be readily carried out in an aqueous or an aqueous/organic co-solvent reaction system wherein the amine equivalent weight of silicone fluid reactant is in the range up to about 2,000. Reactions will go to completion as demonstrated by homogeneity of the reaction mixture. When the amine equivalent weight of the silicone reactant is greater than about 1,200 to 2,000, the reactants are partially or completely insoluble in the reaction system and an incomplete reaction will result unless a co-solvent is used as referenced above. With silicone-containing amidoamine reactants having amine equivalent weights above about 2,000 to about 6,000, the addition of a co-solvent to an aqueous reaction system will not increase the solubility of the reactants as evidenced by phase separation and/or other signs of incomplete reaction.

Surprisingly and unexpectedly, it has been found that alternate embodiments of the phospholipid compositions of the invention can be prepared in substantially completely soluble reaction systems using amidoamine functional silicone reactants as herein described having amine equivalent weights in excess of about 2,500 to about 6,000, or even greater, by also incorporating in the reaction system organic tertiary amine and/or preferably organic amidoamine reactants as herein described, in conjunction with the functional amidoamine silicone reactants. Suitable organic tertiary amino and/or amidoamine-containing reactants are added to the reaction system as a partial replacement of a substantially molar equivalent amount of the functional amidoamine silicone reactant, thus substantially maintaining the above noted molar equivalent ratios of amine reactants to phosphate ester halide reactants in the reaction mixture.

Organic amidoamine intermediate reactants suitable for use in preparing the phospholipid compositions of the invention can be prepared as follows:

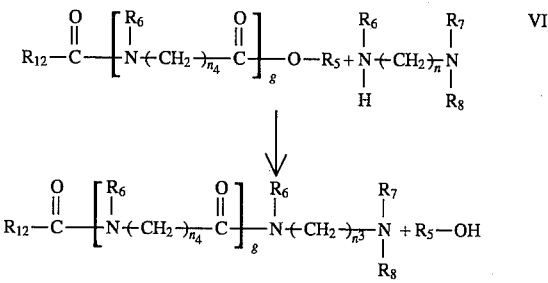

wherein:

$R_{12}$ is alkyl, alkenyl, alkoxy or hydroxyalkyl of from 5 to 21 carbon atoms each alkaryl or aryl up to 20 carbon atoms;

$R_6$ is hydrogen or alkyl, hydroxyalkyl or alkenyl of up to 6 carbon atoms, cycoalkyl of up to 6 carbon atoms, or polyoxalkylene of up to 10 carbon atoms, preferably of from 2 to 5 carbon atoms, within the oxyalkylene unit;

$R_7$ and $R_8$ is as hereinabove defined;

$R_5$ is hydrogen or alkyl;

$g$ is 0 or 1;

$n^3$ is an integer from 2 to 12; and $n^4$ is 1 or greater.

The organic amidoamines suitable for use as intermediate reactants in preparing the phospholipid compositions are known or are generally prepared in accordance with conventional techniques such as shown in the above coupling reaction (VI). A variety of commercially available tertiary amino alkyl amines are suitable for use in reaction with an acid or acid derivative to prepare suitable amidoamines, as are the amidoamines themselves. Suitable tertiary amino alkyl amines can be primary or secondary amines with the proviso that the total number of carbons in the acid portion of the molecule be greater than 6, i.e. to give a hydrophobic moiety necessary for surface activity properties. Suitable amidoamines may be derived from acyl derivatives of aminoacid products such as glycine and sarcosine (N-methylglycine) including for example, products available under the Tradename HAMPOSYL from the Hampshire Chemical Co.

Organic tertiary amine reactants also suitable for use in preparing the phospholipid compositions of the invention can be prepared using procedures well known in the art and many suitable compositions are available.

Exemplary tertiary amines include:

tributylamine
bis(hydroxyethyl)hexylamine
bis(2-hydroxyethyl)cocoamine
N,N-dimethyl-dodecylamine
N,N-dimethyl-tetradecylamine
N,N-dimethyl-hexadecylamine
N,N-dimethyl-cocoamine
N,N-dimethyl-cetylamine dimethyl ($C_{8-16}$) alkyl amine.

N,N-dimethyl-octadecylamine

The reaction of a combination of organic tertiary amine and/or preferably organic amidoamine reactant(s) and silicone-containing amidoamine reactants with phosphate, phosphite and/or polyphosphate ester halide reactants will proceed to completion at an elevated temperature, preferably a temperature ranging from about 75° C. to 95° C., with the formation of the silicone-containing phospholipid compositions of the invention. In a particularly preferred embodiment, when using a silicone-containing amidoamine reactant having an amine equivalent weight in excess of about 4,000, preferably, the organic amidoamine reactant to be used is an N-acylated amidoamine reactant derived from an amino acid or a mixture of such N-acylated amidoamine and an organic amidoamine reactant wherein the amount of N-acylated amidoamine used should be in excess of the stoichiometric amount of total amine reactants required. In general, the amount of said N-acylated amidoamine reactant to be used should be in a range of from about 25 to about 200, preferably 50 to 150, mole percent excess of the total stoichiometric amine reactant used in the coupling reaction. The order of addition of the reactants is not critical although it may be advantageous to add the excess amount of N-acylated amidoamine reactant derived from an amino acid after all the other ingredients have been added. While a heterogeneous mixture may result when all reactants are admixed, the reaction system becomes homogenous as the reaction proceeds. The reaction may start slowly while the mixture is heterogeneous but the reaction mixture will become substantially clear as the reaction proceeds. In accordance with the process of the invention, silicone-containing phospholipid compositions which contain at least weight percent to about 70 weight percent of the silicone composition portion of the total solids of the reaction product can be prepared, which silicone-containing phospholipid compositions will be completely soluble in aqueous/solvent or, preferably, aqueous systems while exhibiting surface active properties including low surface tension, high foaming and substantivity characteristics, low ocular and skin irritation and the like. Thus, it is possible by choice of particular amidoamine functional silicone, organic amidoamine and/or tertiary amine and phosphate ester halide reactants to obtain soluble and, preferably, aqueous soluble silicone-containing phospholipid composition with a wide range of surface active agent properties suitable for use in a variety of applications.

The novel silicone-containing phospholipid compositions of the invention are good surfactants and exhibit good foam volume with excellent foam stability. Moreover, the novel phospholipid compositions are non-irritating to the eyes and skin, are highly substantive to fiber as well as a variety of other characteristics making them well suited for personal care and home care applications.

The preparation of specific compositions of the invention is illustrated by the following specific examples which are provided herein for purposes of illustration only and are not intended to limit the scope therein.

EXAMPLE 1

An alpha-omega bis primary amino alkyl diamino functional polysiloxane fluid obtained commercially under the designation Tegomer A-Si2120 from Goldschmidt Company is used in this example. The amine content of the fluid is 3.5% which corresponds to a molecular weight of 914.

91.4 grams of the above polysiloxane fluid (0.1 moles) is admixed with 26 grams (0.2 moles) of Itaconic Acid in a reaction vessel. Upon combination of the reactants, a heterogeneous mixture is formed. External heat is applied to the reaction vessel bringing the reaction mixture to a temperature of about 110° C., whereupon the reaction mixture becomes completely homogeneous while the temperature rises to 140° C.

After a heating period of 4 hours, a total of 7 ½ ml. of volatiles are collected. The acid value of the reaction mixture is 81.6 (theoretical 95.5) while the alkali number is nil, thus confirming that there is the presence of carboxyl groups on the product.

EXAMPLE 2

An alpha, omega-Bis primary amino alkyl dimethyl polysiloxane fluid with an average molecular weight about 1579.5 and having the general formula:

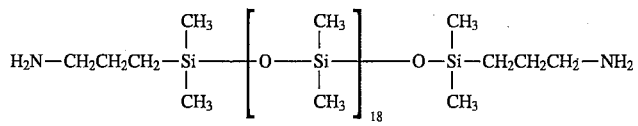

obtained commercially from Shin-Etsu under the designation X-22161A is used in this example.

A mixture of 994.5 grams of the above polysiloxane fluid (0.6296 moles) and 163.7 grams (1.25 moles) of Itaconic Acid is formed in a reaction vessel and heated (slowly to about 90° C. at which point an exotherm occurs raising the reaction vessel temperature to 130° C. and water starts to evolve.

The reaction mixture is heated to and maintained at a temperature of 140° C. to 150° C. for a period of 3 hours during which time about 20 ml. of water and other volatiles are collected. A clear, yellow viscous liquid is formed having an alkali number of 0.

The mixture is then cooled to 90° C. and 192.6 grams (an excess) of dimethylamino propylamine is admixed therewith. The temperature in the reaction vessel is increased to 170° C. to 185° C. and maintained at that temperature for an 4 additional hours during which time a total of 92 ml. of volatiles is collected.

The reaction mixture is then cooled to about 50° C. and subjected to a vacuum of 30 mm. While the vacuum is slowly drawn to 3 mm, the reaction vessel temperature is increased from 75° C. to 150° C. The product residue is then collected from the reaction vessel a 92% yield with an alkali number of 67 (theoretical alkali number is 57).

200.88 grams of the reaction product above (0.12 moles) is then admixed with 75.4 grams of 40% active phosphate ester halide reactant and a 2:1 mixture of propylene glycol and water to obtain a solution having 30% solids. The phosphate ester halide reactant used is prepared by the reaction of 3 moles of epichlorohydrin and one mole of sodium dihydrogen phosphate.

The reaction admixture is heated for 4 hours at a temperature range of 75° C. to 85° C. whereupon a homogeneous, clear liquid solution is obtained having a NaCl content of 1.8% (theoretical NaCl is 1.86%).

The product formed when mixed with water produced a great deal of stable foam whereas the polysiloxane functional amino fluid used as a starting material in the example provided no foam when mixed with water.

EXAMPLE 3

Another sample of a diamino polysiloxane fluid such as used in example 2 is used in this example. The average molecular weight of the sample is 1729 which corresponds to a percent amine of 1.85%.

To 43.2 grams (0.025 moles) of the above siloxane fluid in a reaction vessel is added with mixing 6.5 grams (0.05 moles) of Itaconic acid. The mixture is heated to 90° C. whereupon an exotherm occurs raising the temperature to 130° C. and resulting in a liquified viscous yellow mass. The reaction mixture is heated to and maintained at a temperature of 135°–140° C. for 3 hours while some volatiles are collected and at which point the alkali number is zero.

There is then added to the reaction mixture 7.7 grams (0.075 moles, 50% excess) of dimethylamino propylamine (DMAPA) and the temperature is raised to 165° C. where it is held for four additional hours. The reaction mixture is subjected to vacuum stripping to remove excess DMAPA at a reaction vessel temperature of 125° C. and a vacuum of 10 mm. The alkali number of the reaction product residue is 54 (theoretical 52.9).

A combination of 21.2 grams (0.01 moles) of the reaction product above, 6.25 grams (0.0061 mole) of 40% active phosphate ester halide reactant prepared as in example 2, 16 grams of isopropanol and 16 grams of water having a solid content of 40% is prepared in a reaction vessel. The combined reactants are heated to a temperature of 95° C. for four-five hours at which time a clear yellow solution is obtained having a NaCl content of 2.4% (theoretical 1.9%).

The product formed when added to water produces a great deal of stable foam.

EXAMPLE 4

A pendant (lateral) amino functional silicone fluid having an average molecular weight of 4400 obtained from Shin-Etsu under the product designation KF865 is used in this example.

88 grams (0.02 moles) of the silicone fluid is admixed with 2.6 grams of Itaconic acid (0.02 moles) and heated to a temperature of 130°–140° C. whereupon a clear melt is obtained and then continued heating for an additional two hours.

After heating for two hours, the reaction mixture is cooled to 70° C. and 4.08 grams (an excess) of dimethylamino propyl amine (DMAPA) is admixed therewith. The reaction mixture is then heated to a temperature of 165° C. for four hours, cooled to 70° C. and vacuum stripped at 30–10 mm for three hours while slowly raising the temperature to 110° C.

The reaction product residue is a clear liquid having an alkali number of 12.3 (theoretical 12.2) and an acid number of 0. I.R. analysis confirms the presence of an amide linkage.

EXAMPLE 5

A pendant (lateral) aminofunctional silicone fluid obtained from Shin-Etsu under the product designation KF 865 is used in this example. The silicone fluid has an amine value of 0.2219 percent which corresponds to an amine equivalent weight of 5675.

665.9 grams (0.1173 equiv. wt.) of the silicone fluid and 15.25 grams of Itaconic acid (0.1173 mole) are combined with 150 ml of xylene in a reaction vessel and heated to a temperature of 130°–140° C. under reflux. After heating for 4 to 5 hours under reflux, 2.3 ml of water is removed (theory 2.1).

17.9 grams of dimethylpropyl amine (DMAPA) is then admixed with the reaction mixture and heated under reflux at a temperature of 160°–170° C. for a period of about 4 hours during which time an additional 2.1 grams of water is removed. The reaction mixture is cooled to about 70° C. and vacuum stripped at 30–40 mm to remove low boiling volatiles. A vacuum of 5–10 mm is then applied to the reaction mixture and the reaction vessel is heated for three hours at 140° C. The reaction product is a clear liquid having an alkali number of 9 (theoretical 9.55) which corresponds to an amine equivalent weight of 6233.

264 grams (0.9428 moles) of cocoyl sarcosine obtained as HAMPOSYL C from Hampshire Chemical Corp. is reacted in another reaction vessel with 144 grams (an excess) of dimethylaminopropyl amine in 150 ml of refluxing xylene under a nitrogen atmosphere, with water being removed as it is formed. After 4 hours, water no longer evolves and the xylene and any volatiles are removed by heating the reaction mixture to 130° C. at 10 mm vacuum for 3 hours. 348 grams of a product having an alkali number of 185 is obtained.

12.4 grams (0.002 equiv. wt.) of the above silicone/DMAPA product are combined with 2.4 grams (0.008 moles) of the above sarcosine/DMAPA product; 3.12 grams (0.0033 moles) of a 40% concentration of a phosphate ester halide reactant prepared by the reaction of 3 moles of epichlorohydrin with one mole of 85% phosphoric acid in the presence of one mole sodium hydroxide and 36 ml water in a reaction vessel. The reactant mixture is heated for 4 hours at a temperature of 85°–90° C. The reaction mixture is hazy and non-homogeneous. Upon the addition of 2.67 grams (0.009 mole) additional grams of the sarcosine/DMAPA, the reaction mixture immediately becomes clear and homogeneous. The silicone content of the reaction product based on the total solids is 64%. The product when added to water produces a great deal of stable foam.

EXAMPLE 6

A mixture of the silicone/DMAPA and the 40% active solution of chlorohydroxy propyl phosphate reactants of example 5 when charged to a reaction vessel forms a completely non-homogeneous mixture even when heated at 100° C. for several hours with only oily phases coating the reaction vessel.

EXAMPLE 7

The silicone/DMAPA, cocoyl sarcosine DMAPA and phosphate ester reactants of example 5 are used in this example.

A combination of 18.7 grams (0.003 equiv.) of silicone/DMAPA; 2.12 grams (0.007 equiv.) of sarcosine/DMAPA; 3.12 grams of phosphate ester halide and 50 grams of water is formed in a reaction vessel and heated to 85°–90° C. for 3 hours. The reaction mixture becomes thick and difficult to agitate with only a small liquid phase. There is now added to the reaction mixture 20 grams of water and 5 grams (0.016 equiv.) of the cocoylsarcosine/DMAPA and the reaction mixture is heated for two additional hours. A homogenous, clear solution results having a silicone solid content of 69%.

19
EXAMPLE 8

DiSodium 1, 3 Bis 3 chloro-2 hydroxy propyl pyrophosphate is prepared by charging 446 parts of $Na_4P_2O_7 \cdot 10H_2O$ (1 mole) and 178 parts $H_4P_2O_7$ (1 mole) with 1000 parts deionized water to a reaction vessel and reacting the same with 320 parts epichlorohydrin at 60°–80° C. for 3–4 hours. 81.4 parts (0.2 equivalents) of the above reaction product is combined with a mixture of a pendant trimethylsilyl silicone pyrrolidone containing amidoamine having an equivalent weight of 1845 (0.05 equivalent) and 57.6 parts of N-Dimethylaminopropyl linoleamide (0.15 equivalents) and then diluted with 480 grams of water to a 30% concentration. After the solution is adjusted to a pH of 8, the reaction mixture is heated to 90°–95° for a period of 4–5 hours at which time a clear solution forms. The reaction is monitored via argentometric estimation for covalent chloride to ionic chloride and the reaction is completed in 5 hours.

The reaction product foams well in water.

EXAMPLE 9

A 3-chloro-2 hydroxypropylester salt of phosphorous acid is prepared by charging 41 grams (0.5 mole) of phosphorus, 409 grams of water and 50 grams of 50% NaOH solution (0.6 mole) to a reaction vessel and warmed to 75° C. 46,25 grams (0.5 mole) of epichlorohydrin is then added and the reaction mixture is heated to 75° C. for 1½ hours with stirring.

196 parts of the combined epichlorohydrinphosphite reaction mixture is admixed with 50% sodium hydroxide solution to achieve a pH of 8 followed by adding the combination of a pendant trimethylsilyl capped pyrrolidone containing silicone amidoamine having an equivalent weight of 3500 and 27.3 parts of cocoyl safcosine amidoamine (0.09 equivalents). The reaction mixture is diluted with water to achieve 25% solids.

The reaction mixture is heated to 90° C. for 2 hours whereupon a clear aqueous solution is formed.

EXAMPLE 10

3-Bromopropyl diacid phosphate ($BrCH_2CH_2CH_2OPO(OH)_2$) is prepared by reacting 3-Bromopropyl with $POCl_3$ while utilizing one equivalnet of triethyamine in the methylene chloride solvent. The Dichloride is isolated and hydroyzed to the diacid with water. The pH of the product in water is adjusted to 8 followed by the addition of an equivalent amount of 50:50 combination of a trimethylsilyl capped pyrrolidone containing silicone amidoamine having an equivalent weight of 1845 and N-Dimethyl aminopropyl derivative of linoleamide. The reaction mixture is adjusted with water to 30% of total solids.

The reaction mixture is heated for 4 hours at 90° C. A clear solution is formed.

Although some preferred embodiments have been described, many modifications and variations may be made thereto in light of the above teachings. It is therefore to be understood that within the scope of the appended claims, the invention may be practiced otherwise than as specifically described and illustrated.

What is claimed is:

1. A silicone-containing phospholipid composition having the general formula:

20

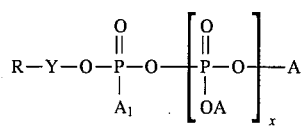

wherein:
A is selected from H, M or R—Y—;
$A_1$ is selected from H, OH, OM or R—Y—O—;
M is a cation;
Y is substituted or unsubstituted alkylene optionally interrupted by up to 3 oxygen atoms;
x is 0 or an integer from 1–5; and
R is a quaternized organosilicone amidoamine reactant moiety of the formula:

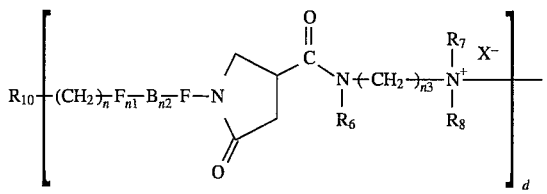

wherein:
$R_{10}$ is the silicone backbone chain to which at least one pyrrolidone containing amidoamine functional group is attached;
$R_6$ is hydrogen or alkyl, hydroxyalkyl or alkenyl of up to 6 carbon atoms each, cycloalkyl of up to 6 carbon atoms, or polyoxyalkylene of up to 10 carbon atoms within the oxyalkylene unit;
$R_7$ and $R_8$, which may be the same or different, are selected from alkyl, hydroxyalkyl, carboxyalkyl of up to 6 carbon atoms in each alkyl moiety or polyoxyalkylene of up to 10 carbon atoms; or in addition $R_7$ and $R_8$ taken together with the nitrogen to which they are attached represents an N-heterocycle;
F which can be the same of different is linear or branched alkylene of 1–12 carbon atoms;
$X^-$ is an anion;
n is 0 or 2;
$n^1$ is 0 or 1;
$n^2$ is 0 or 1;
$n^3$ is an integer from 2 to 12;
B is —$NR_{11}$ sulfur or oxygen, wherein $R_{11}$ is hydrogen or lower alkyl ($C_{1-6}$); with the proviso that when $n^1$ is 0 and $n^2$ is 1, $n^1$ is 1, when n is 2 and $n^2$ is 1, $n^1$ is 0 or 1 and when n is 2 and $n^2$ is 0, $n^1$ is 0; and;
d is one or greater.

2. The silicone-containing phospholipid composition as claimed in claim 1, wherein $R_{10}$ is a polysiloxane backbone chain to which at least one pyrrolidone containing amidoamine functional group is attached, said polysiloxane backbone chain having the formula:

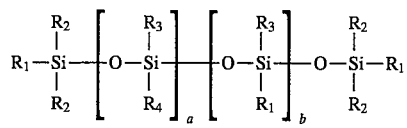

wherein:
$R_1$ can be the same or different and is selected from $R_2$, a primary amine or a pyrrolidone containing carboxyl functional group or amidoamine derivative thereof; with the proviso that at least one of $R_1$ is a pyrrolidone containing amidoamine functional group, $R_2$ can be the same or different and is selected from alkyl, aryl or olefinic;

$R_3$ and $R_4$, which may be the same or different are selected from alkyl, aryl, capped or uncapped polyoxyalkylene, alkaryl, aralkylene or alkenyl;

e is an integer from 0 to 50,000;

f is an integer from 0 to 100.

3. The silicone-containing phospholipid composition as claimed in claim 2, wherein f is 0.

4. The silicone-containing phospholipid composition as claimed in claim 2, wherein the terminal groups $R_1$ are $R_2$ and e and f are each at least 1.

5. The silicone-containing phospholipid composition as claimed in claim 1, wherein M is an alkali metal, $X^-$ is a halogen, and d is an integer from 2 to 10.

6. Silicone-containing phospholipid compositions having the following general formula:

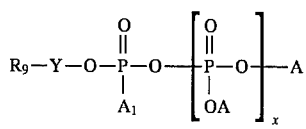

wherein:

A is selected from H, M or $R_9$—Y—;

$A_1$ is selected from H, OH, OM or R—$_9$—Y—O$^-$;

M is a cation;

x is 0 or an integer from 1 to 5;

Y is alkylene or substituted alkylene; and $R_9$ is a mixture of a quaternized silicone-containing amidoamine moiety of the formula a) and a member selected from the group consisting of an organic amidoamine moiety of the formula b), an organic tertiary amine moiety of the formula c) and mixtures of the same a) a quaternized organosilicone amidoamine moiety of the formula:

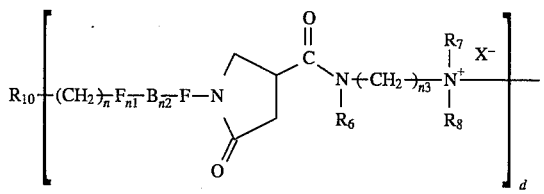

wherein:

$R_{10}$ is a silicone backbone chain to which at least one pyrrolidone containing amidoamine functional group is attached;

$R_6$ is hydrogen, alkyl, hydroxyalkyl, alkenyl of up to 6 carbon atoms each, cycloalkyl of up to 6 carbon atoms, or polyoxyalkylene of up to 10 carbon atoms within the oxyalkylene unit;

$R_7$ and $R_8$, which may be the same or different, are selected from alkyl, hydroxyalkyl, carboxyalkyl of up to 6 carbon atoms in each alkyl, or polyoxyalkylene of up to 10 carbon atoms; or in addition $R_7$ and $R_8$ taken together with the nitrogen to which they are attached represent an N-heterocycle;

$X^-$ is an anion;

n is 0 or 2;

$n^1$ 0 or 1;

$n^2$ is 0 or 1;

$n^3$ is an integer from 2 to 12;

B is —$NR_{11}$, sulfur (S) or oxygen (O), wherein $R^{11}$ is hydrogen or lower alkyl ($C_{1-6}$); with the proviso that when n is 0 and $n^2$ is 1, $n^1$ is 1, when n is 2 and $n^2$ is 1, $n^1$ is 0 or 1 and when n is 2 and $n^2$ is 0, $n^1$ is 0; and d is one or greater;

b) a quaternized organic amidoamine moiety of the formula:

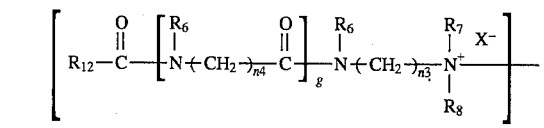

wherein:

$R_{12}$ is alkyl, alkenyl, alkoxy or hydroxyalkyl of from 5 to 21 carbon atoms each, alkaryl or aryl of up to 20 carbon atoms;

R6 is hydrogen, alkyl, hydroxyalkyl or alkenyl of up to 6 carbon atoms each, cycoalkyl of up to 6 carbon atoms, or polyoxyalkylene of up to 10 carbon atoms within the oxyalkylene unit;

$R_7$ and $R_8$ which may be the same or different, are selected from alkyl, hydroxyalkyl, carboxyalkyl of up to 6 carbon atoms in each alkyl, or polyoxyalkylene of up to 10 carbon atoms; or in addition $R_7$ and $R_8$ taken together with the nitrogen to which they are attached may represent an N-heterocycle;

$X^-$ is an anion;

g is 0 or 1;

$n^3$ is integer from 2 to 12; and $n^4$ is 1 or greater; or c) an organic quaternized tertiary amine moiety of the formula:

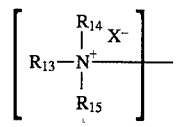

wherein:

$R_{13}$, $R_{14}$ and $R_{15}$ are the same or different and are alkyl, substituted alkyl, alkylaryl or alkenyl groups of up to 16 carbon atoms with the proviso that the total carbon atoms in $R_{13}$+$R_{14}$+$R_{15}$ is between 10 and 24;

$X^-$ is an anion;

with the proviso that at least 5 equivalent weight percent to about 70 equivalent weight percent of the total equivalent weight of amine moieties of the phospholipid composition is a quaternized organosilicone amidoamine moiety.

7. The silicone-containing phospholipid compositions as claimed in claim 6, wherein $R_9$ is a mixture of;

a) quaternized organosilicone amidoamine moieties of the formula:

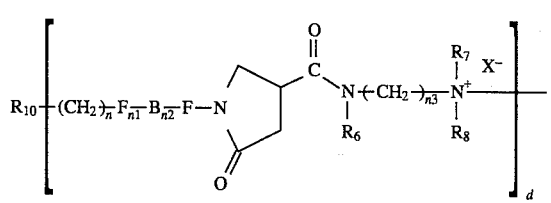

and

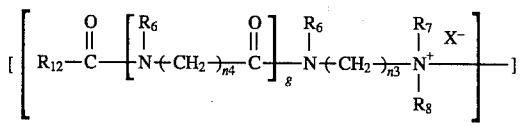

b) quaternized organic amidoamine moieties of the formula:

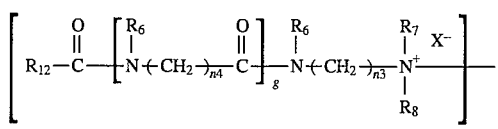

wherein:

$R^1$ can be the same or different and is selected from $R_2$, a primary amine or a pyrrolidone containing carboxyl functional group or amidoamine derivative thereof; with the proviso that at least one of $R_1$ is a pyrrolidone containing amidoamine functional group;

$R_2$ can be the same or different and is selected from alkyl, aryl or olefinic;

$R_3$ and $R_4$, which may be the same or different are selected from alkyl, aryl, capped or uncapped polyoxyalkylene, alkaryl, aralkylene or alkenyl;

e is an integer from 0 to 50,000;

f is an integer from 0 to 100.

8. The phospholipid compositions as claimed in claim 7, wherein $R_{10}$ is a silicone backbone chain to which at least one pyrrolidone containing amidoamine functional group is attached, said polysiloxane backbone chain having the formula:

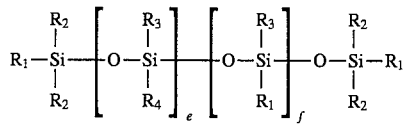

wherein:

$R_1$ can be the same or different and is selected from $R_2$, a primary amine or a pyrrolidone containing carboxyl functional group or amidoamine derivative thereof; with the proviso that at least one of $R_1$ is a pyrrolidone containing amidoamine functional group;

$R_2$ can be the same or different and is selected from alkyl, aryl or olefinic;

$R_3$ and $R_4$, which may be the same or different are selected from alkyl, aryl, capped or uncapped polyoxyalkylene, alkaryl, aralkylene or alkenyl;

e is an integer from 0 to 50,000;

f is an integer from 0 to 100.

9. The phospholipid compositions as claimed in claim 6, wherein g in the quaternized organic amidoamine moiety b) is 1.

10. The phospholipid composition, as claimed in claim 7, wherein g in the quaternized organic amidoamine moiety b is 1.

11. The phosphilipd compositions as claimed in claim 8, wherein f is 0.

12. The phospholipid compositions as claimed in claim 8, wherein the terminal groups $R_1$ are $R_2$ and e and f are each at least 1.

13. The phospholipid compositions as claimed in claim 8, wherein $R_2$, $R_3$ and $R_4$ are each methyl.

14. A method of preparing phospholipid compositions represented by the general formula:

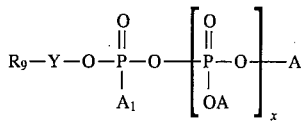

wherein:

A is selected from H, M or $R_9$—Y—;

$A_1$ is selected from H, OH, OM or $R_9$—Y—O$^-$;

M is a cation;

x is 0 or an integer from 1 to 5;

Y is alkylene or substituted alkylene; and $R_9$ is a mixture of a quaternized silicone-containing amidoamine moiety and a member selected from an organic amidoamine or tertiary amine moieties;

which comprises reacting the combination of a member selected from an organic amidoamine or an organic tertiary amine reactant or mixtures of the same and a silicone-containing pyrrolidone-containing amidoamine reactant with a phosphate, phosphate or polyphosphate ester reactant in the equivalent weight ratios of from about 0.7 to 3.3 of total amidoamine and/or tertiary amine reactants to 1 of phosphate, phosphite or polyphoshate ester reactant until the amine reactant is substantially completely reacted, with the proviso that at least 5 equivalent weight percent to about 70 equivalent weight percent of the total equivalent weight of amine reactants will be silicone containing, said phosphate ester reactant being of the general formula:

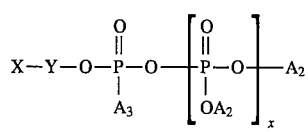

wherein:

$A_2$ is selected from H, M or X—Y—;

$A_3$ is selected from H, OH, OM or X—Y—O$^-$;

M is a cation;

Y is alkylene or substituted alkylene;

X is halogen; and x is 0 or an integer from 1 to 5.

15. The silicone-containing phospholipid composition as claimed in claim 1, wherein Y is 2 hydroxy propylene.

16. The silicone-containing phospholipid composition as claimed in claim 1 wherein Y is substituted with lower alkyl or alkoxyalkyl, with not more than 10 carbon atoms each, or with hydroxy.

17. The silicone-containing phospholipid compositions as claimed in claim 6, wherein Y is 2 hydroxy propylene.

* * * * *